United States Patent [19]

Knudsen

[11] Patent Number: 5,173,105
[45] Date of Patent: Dec. 22, 1992

[54] CERTAIN SUBSTITUTED BIS(2-BENZOYL-3-OXO-CYCLOHEXENYL)-DIAMINES

[75] Inventor: Christopher G. Knudsen, Berkeley, Calif.

[73] Assignee: Imperial Chemical Industries Plc, London, England

[21] Appl. No.: 650,525

[22] Filed: Feb. 5, 1991

[51] Int. Cl.$^5$ .................. A01N 41/10; C07C 317/06
[52] U.S. Cl. .......................... 71/103; 71/98; 71/105; 71/111; 71/112; 71/118; 71/121; 558/418; 558/419; 560/147; 560/150; 560/159; 564/82; 564/85; 564/86; 564/154; 564/155; 564/157; 564/221; 564/306
[58] Field of Search ............ 564/452, 440, 82, 85, 564/86, 88, 89, 154, 155, 157, 221; 71/121, 123, 103; 558/418, 419

[56] References Cited

U.S. PATENT DOCUMENTS 4,775,441 10/1988 Knudsen .................. 71/121

OTHER PUBLICATIONS

Royal Society of Chemistry, "The Agrochemicals Handbook" 2nd Ed. 1987.
Y. Tamura et al: "Photochemical Dealkylation of 2-Acyl-3-Alkylamino-5,5-Dimethyl-2-Cyclohexen-1-Ones", Chemical and Pharmaceutical Bulletin, vol. 30, No. 5, pp. 1692–1696 (1982), Tokyo, Japan.

Primary Examiner—Carolyn Elmore
Assistant Examiner—B. Burn
Attorney, Agent, or Firm—William E. Dickheiser

[57] ABSTRACT

An herbicide compound of the formula wherein

R is halogen, $C_1$-$C_2$ alkyl, $C_1$-$C_2$ alkoxy, nitro; cyano; $C_1$-$C_2$ haloalkyl, or $R^aSO_n$— wherein n is 0 or 2 and $R^a$ is $C_1$-$C_2$ alkyl;

$R^1$ is hydrogen or $C_1$-$C_4$ alkyl;

$R^2$ is hydrogen or $C_1$-$C_4$ alkyl; or $R^1$ and $R^2$ together are alkylene having 2 to 5 carbon atoms;

$R^3$ is hydrogen or $C_1$-$C_4$ alkyl;

$R^4$ is hydrogen or $C_1$-$C_4$ alkyl; or $R^3$ and $R^4$ together are oxo;

$R^5$ is hydrogen or $C_1$-$C_4$ alkyl;

$R^6$ is hydrogen or $C_1$-$C_4$ alkyl; or $R^5$ and $R^6$ together are alkylene having 2 to 5 carbon atoms;

$R^7$ and $R^8$ independently are (1) hydrogen; (2) halogen; (3) $C_1$-$C_4$ alkyl; (4) $C_1$-$C_4$ alkoxy; (5) trifluoromethoxy; (6) cyano; (7) nitro; (8) $C_1$-$C_4$ haloalkyl; (9) $R^bSO_n$— wherein n is the integer 0, 1 or 2; and $R^b$ is (a) $C_1$-$C_4$ alkyl; (b) $C_1$-$C_4$ alkyl substituted with halogen or cyano; (c) phenyl; or (d) benzyl; (10) —$NR^cR^d$ wherein $R^c$ and $R^d$ independently are hydrogen or $C_1$-$C_4$ alkyl; (11) $R^eC(O)$— wherein $R^e$ is $C_1$-$C_4$ alkyl or $C_1$-$C_4$ alkoxy; (12) $SO_2NR^cR^d$ wherein $R^c$ and $R^d$ are as defined; (13) —$N(R^c)C(O)R^d$ wherein $R^c$ and $R^d$ are as defined; or (14) —$CH_2CH_2OCH_3$ or —$CH_2CH_2OC_2H_5$; with the proviso that $R^7$ is not at the 6-position; and $R^9$ is hydrogen or $C_1$-$C_4$ alkyl; and $R^{10}$ is $C_2$-$C_6$ alkylene, $C_4$-$C_8$ alkenylene or $C_4$-$C_8$ alkynylene.

31 Claims, No Drawings

CERTAIN SUBSTITUTED BIS(2-BENZOYL-3-OXO-CYCLOHEXENYL)DIAMINES

BACKGROUND OF THE INVENTION

Herbicidal compounds having the structural formula

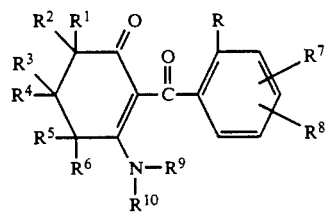

wherein R through $R^9$ are as defined below and $R^{10}$ is (a) hydrogen, (b) $C_1$-$C_6$ alkyl, (c) $C_4$-$C_6$ cycloalkyl, (d) substituted $C_1$-$C_6$ alkyl, (e) phenyl, (f) substituted phenyl, (g) $C_1$-$C_6$ alkoxy, (h) benzyl, (i) phenethyl, (j) $C_1$-$C_4$ alkyl—C(O)—, (k) $C_1$-$C_4$ alkyoxy—C(O)—, (l) $C_2$-$C_6$ alkenyl, or (m) $C_2$-$C_6$ alkynyl; are described in U.S. Pat. No. 4,775,411 which is incorporated herein by reference.

DESCRIPTION OF THE INVENTION

This invention relates to certain substituted bis(2-benzoyl-3-oxo-cyclohexenyl)diamines and their use as herbicides.

One embodiment of this invention is an herbicidal composition comprising an herbicidally active substituted bis(2-benzoyl-3-oxo-cyclohexenyl)diamines and an inert carrier therefor wherein the 2-position of each benzoyl moiety is substituted as herein recited and the 4-position preferably is substituted with an electron withdrawing group such as halogen, cyano, trifluoromethyl or nitro. The 4-, 5- and 6-positions of each cyclohex-2-enone moiety can be substituted, preferably with the groups hereinafter recited. More preferably, the cyclohex-2-enone moieties have no substitution or the 4- or 6-positions are substituted with one or two methyl groups. The 3-, 4- and 5-positions of the benzoyl moieties can be substituted, preferably with the groups hereinafter recited.

Also embodied within the scope of this invention are novel compounds having the following structural formula

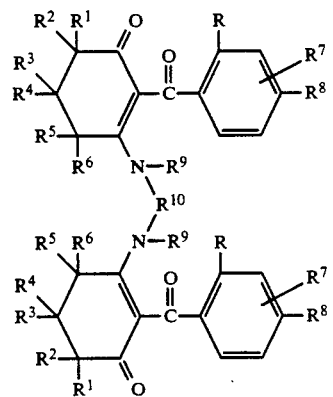

R is halogen; $C_1$-$C_2$ alkyl, preferably methyl; $C_1$-$C_2$ alkoxy, preferably methoxy; nitro; cyano; $C_1$-$C_2$ haloalkyl, preferably trifluoromethyl; or $R^aSO_n$—wherein n is 0 or 2, preferably 2 and $R^a$ is $C_1$-$C_2$ alkyl, preferably methyl. Preferably, R is chlorine, bromine, $C_1$-$C_2$ alkyl, $C_1$-$C_2$ alkoxy, cyano, nitro, $C_1$-$C_2$ alkylthio or $C_1$-$C_2$ alkylsulfonyl; more preferably chlorine, nitro, methyl, trifluoromethyl or methylsulfonyl;

$R^1$ is hydrogen or $C_1$-$C_4$ alkyl, preferably $C_1$-$C_2$ alkyl, more preferably methyl, most preferably $R^1$ is hydrogen or methyl;

$R^2$ is hydrogen; $C_1$-$C_4$ alkyl, preferably $C_1$-$C_2$ alkyl, more preferably methyl, most preferably $R^2$ is hydrogen or methyl; or $R^1$ and $R^2$ together are alkylene having 2 to 5 carbon atoms;

$R^3$ is hydrogen or $C_1$-$C_4$ alkyl, preferably $C_1$-$C_2$ alkyl, more preferably methyl, most preferably $R^3$ is hydrogen or methyl;

$R^4$ is hydrogen or $C_1$-$C_4$ alkyl, preferably $C_1$-$C_2$ alkyl, more preferably methyl, most preferably $R^4$ is hydrogen or methyl; or $R^3$ and $R^4$ together are oxo;

$R^5$ is hydrogen or $C_1$-$C_4$ alkyl, preferably $C_1$-$C_2$ alkyl, more preferably methyl, most preferably $R^5$ is hydrogen or methyl;

$R^6$ is hydrogen or $C_1$-$C_4$ alkyl, preferably $C_1$-$C_2$ alkyl, more preferably methyl, most preferably $R^6$ is hydrogen; or $R^5$ and $R^6$ together are alkylene having 2 to 5 carbon atoms;

$R^7$ and $R^8$ independently are (1) hydrogen; (2) halogen, preferably chlorine, fluorine or bromine; (3) $C_1$-$C_4$ alkyl, preferably methyl; (4) $C_1$-$C_4$ alkoxy, preferably methoxy or ethoxy; (5) trifluoromethoxy; (6) cyano; (7) nitro; (8) $C_1$-$C_4$ haloalkyl, more preferably trifluoromethyl; (9) $R^bSO_n$—wherein n is the integer 0, 1 or 2, preferably 0 or 2; and $R^b$ is (a) $C_1$-$C_4$ alkyl, preferably methyl; (b) $C_1$-$C_4$ alkyl substituted with halogen, preferably chloromethyl, or trifluoromethyl; (10) —$NR^cR^d$ wherein $R^c$ and $R^d$ independently are hydrogen or $C_1$-$C_4$ alkyl; (11) $R^eC(O)$—wherein $R^e$ is $C_1$-$C_4$ alkyl or $C_1$-$C_4$ alkoxy; (12) —$SO_2NR^cR^d$ wherein $R^c$ and $R^d$ are as defined; (13) —$N(R^c)C(O)R^d$ wherein $R^c$ and $R^d$ are as defined; and (14) —$CH_2CH_2OCH_3$ or —$CH_2CH_2OC_2H_5$; with the proviso that $R^7$ is not in the 6-position; and $R^9$ is hydrogen or $C_1$-$C_4$ alkyl, preferably methyl or ethyl;

$R_{10}$ is $C_2$-$C_6$ alkylene, preferably $C_2$-$C_4$ alkylene, more preferably ethylene; $C_4$-$C_8$ alkenylene or $C_4$-$C_8$ alkynylene, preferably 2-butenylene.

The term "$C_1$-$C_4$ alkyl" includes methyl, ethyl, n-propyl, isopropyl, n-butyl, sec-butyl, isobutyl and t-butyl. The term "halogen" includes chlorine, bromine, iodine and fluorine. The term "$C_1$-$C_4$ alkoxy" includes methoxy, ethoxy, n-propoxy, isopropoxy, n-butoxy, sec-butoxy, isobutoxy and t-butoxy. The term "$C_1$-$C_4$ haloalkyl" includes the alkyl groups defined above under $C_1$-$C_4$ alkyl in which one or more hydrogen is replaced by chloro, bromo, iodo or fluoro.

The term "$C_2$-$C_6$ alkylene" includes ethylene, propylene, and butylene where one or more hydrogen atoms optionally can be replaced with lower an alkyl group. The term "$C_4$-$C_8$ alkenylene" includes 2-butenylene (—$CH_2$—$CH$=$CH$—$CH_2$—) and 2-pentenylene (—$CH_2$—$CH$=$CH$—$CH_2$—$CH_2$—). The term "$C_4$-$C_8$ alkynylene" includes 2-butynylene (—CH$_2$—C≡C—CH$_2$—).

Preferably, R is chlorine, bromine, nitro, methyl or trifluoromethyl, preferably R$^7$ is in the 3-position. More preferably R$^7$ is hydrogen, C$_1$-C$_4$ alkoxy, —CH$_2$CH$_2$OCH$_3$, —CH$_2$CH$_2$OC$_2$H$_5$, or C$_1$-C$_4$ thioalkyl. More preferably, R$^7$ is hydrogen, methylthio, methoxy, ethoxy, —CH$_2$CH$_2$OCH$_3$ or —CH$_2$CH$_2$OC$_2$H$_5$. Most preferably, R$^8$ is halogen, trifluoromethyl, or R$^b$SO$_n$ wherein R$^b$ is C$_1$-C$_4$ alkyl, preferably methyl or ethyl, and n is the integer 0 or 2.

The compounds of this invention are active herbicides of a general type. That is, they are herbicidally effective against a wide range of plant species. The method of controlling undesirable vegetation of the present invention comprises applying an herbicidally effective amount of the above-described compounds to the area where control is desired.

The compounds of the present invention can be prepared by the following two-step general method.

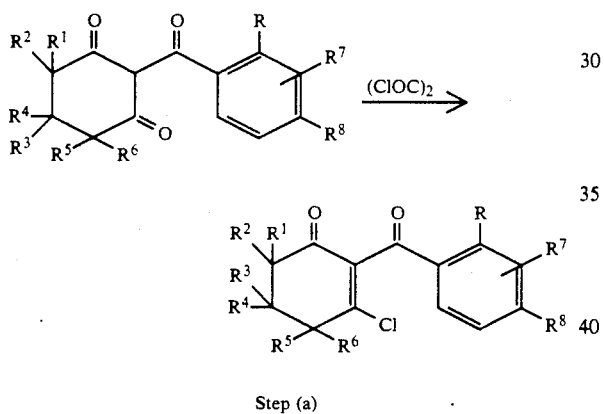

Step (a)

wherein R through R$^8$ are as defined.

Generally, in step (a) the benzoyl dione is dissolved in an inert solvent such as methylene dichloride and an excess, usually 150 to 200 mole percent, of oxalyl chloride is added followed by a catalytic amount (0.1 equivalent) of dimethylformamide. The reaction mixture is stirred from one hour to one day at room temperature. The reaction product is isolated using conventional techniques.

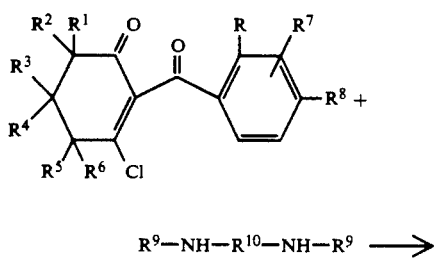

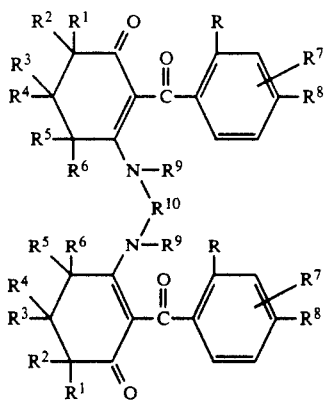

Step (b)

wherein R through R$^{10}$ are as defined.

Generally, in step (b) 2 mole of the 3-chloro-2-benzoylcycloalk-2-enone are reacted with a mole of the diamine and a mole of a non-nucleophilic base such as triethylamine in an inert solvent. The mixture is stirred 1 to 18 hours and the desired product is isolated using conventional techniques.

The following examples teach the synthesis of a representative compound of this invention.

EXAMPLE I

3-Chloro-2-(2-chloro-4-methanesulfonylbenzoyl) cyclohex-2-enone

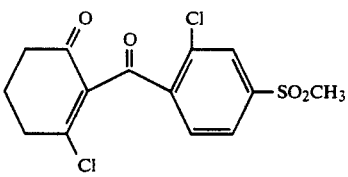

2-(2-Chloro-4-methanesulfonylbenzoyl)-cyclohexane -1,3-dione [9.8 grams (g.), 30 millimole (mmol)] was dissolved in 100 milliliters (ml) methylene chloride and stirred at room temperature. To this solution was added oxalyl chloride (5.7 g., 45 mmol) followed by dimethylformamide (0.5 ml) in portions small enough to control effervescence. The resulting solution was stirred for 4 hours and then poured into water and extracted with methylene chloride. The organic layer was washed again with water, saturated K$_2$CO$_3$ solution and then dried with MgSO$_4$ and the solvent evaporated to yield 3-chloro-2(2-chloro-4-methanesulfonylbenzoyl) cyclohex-2-enone (7.3 g., 70%) as an oil which was used without further purification.

EXAMPLE II

TABLE I

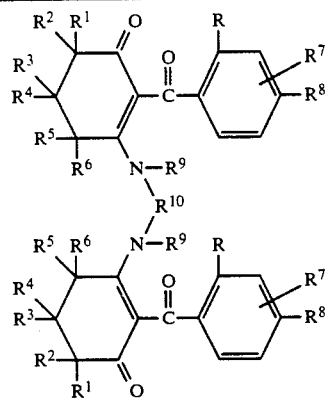

| Cmpd. No. | R | R¹ | R² | R³ | R⁴ | R⁵ | R⁶ | R⁷ | R⁸ | R⁹ | R¹⁰ |
|---|---|---|---|---|---|---|---|---|---|---|---|
| 1. | NO₂ | CH₃ | CH₃ | H | H | H | H | H | 4-SO₂CH₃ | CH₃ | CH₂CH₂ |
| 2. | NO₂ | H | H | H | H | H | H | H | 4-CF₃ | CH₃ | CH₂CH=CHCH₂ |
| 3. | Cl | H | H | CH₃ | H | H | H | 3-OCH₂CH₃ | 4-SO₂CH₂CH₃ | CH₃ | CH₂CH₂ |
| 4.ᵃ⁾ | Cl | H | H | H | H | H | H | H | 4-SO₂CH₃ | CH₃ | CH₂CH₃ |
| 5. | NO₂ | CH₃ | CH₃ | H | H | H | H | H | H | CH₃ | CH₂CH₂ |
| 6. | NO₂ | CH₃ | CH₃ | H | H | H | H | H | 4-SO₂CH₃ | CH₃ | CH₂CH₂CH₂CH₂ |
| 7. | NO₂ | CH₃ | CH₃ | —O— | | CH₃ | CH₃ | H | 4-CF₃ | CH₃ | CH₂CH₃ |

ᵃ⁾Prepared in Example II.

N,N'-dimethyl-N,N'-di
(2-(2-chloro-4-methanesulfonylbenzoyl)-3-oxo-
cyclohexenvl)ethylene diamine

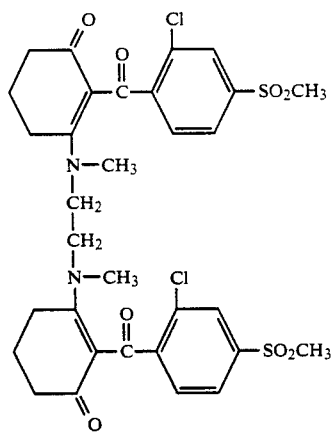

3-Chloro-2-(2-chloro-4-methanesulfonylbenzoyl)-cyclohex-2-enone (1.8 g., 5 millimole) was dissolved in 50 ml of methylene chloride and stirred at room temperature. A mixture of N,N'-dimethylethylene diamine (0.22 g., 2.5 mmol mole) and triethylamine (0.5 g., 5 mml) in 10 ml of methylene chloride was added dropwise over 20 minutes and the resulting solution was stirred for 2 hours. The reaction mixture was poured into IN HCl and extracted with additional methylene chloride. The organic layer was washed with saturated NaHCO₃ solution, dried with MgSO₄ and the solvent evaporated to yield a yellow foam: 1.6 g., 86%. The structure is consistent with nuclear magnetic resonance, infrared and mass spectral data.

The following is a table of certain selected compounds that are preparable according to the procedure described herein. Compound numbers are assigned to each compound and are used throughout the remainder of the application.

Herbicidal Screening Tests

As previously mentioned, the herein described compounds produced in the above-described manner are phytotoxic compounds which are useful and valuable in controlling various plant species. Selected compounds of this invention were tested as herbicides in the following manner.

Pre-emergence Multi-weed Herbicide Test: On the day preceding treatment, seeds of eight different weed species are planted in loamy sand soil in individual rows using one species per row across the width of a flat. The weeds used are green foxtail (FT) (*Setaria viridis*), giant foxtail (GFT) (*Sentenia faberi*), watergrass (WG) (*Echinochloa crusgalli*), broadleaf signalgrass (BSG) (*Brachiaria platyphylla*), annual morning-glory (AMG) (*Ipomoea lacunosa*), cocklebur (CB) (*Xanthium sp.*), velvetleaf (VL) (*Abutilon theophrasti*), and yellow nutsedge (YNS) (*Cyperus esculentus*). Ample seeds are planted to give about 20 to 40 seedlings per row, after emergence, depending upon the size of the plants.

Using an analytical balance, 25 milligrams (mg) of the compound to be tested are weighed out on a piece of glassine weighing paper. The paper and compound are placed in a 60 milliliter (ml) wide-mouth clear bottle and dissolved in a solution of 20 ml of acetone and 20 ml water containing enough polyoxyethylene sorbitan monolaurate emulsifier to give a final solution of 0.5% (v/v). The solution is then sprayed on a seeded flat on a linear spray table calibrated to deliver 400 L/ha. The application rate was 0.25 kg/ha.

After treatment, the flats are placed in the greenhouse at a temperature of 70° to 80° F. and watered by sprinkling. Two weeks after treatment, the degree of injury or control is determined by comparison with untreated check plants of the same age. The injury rating from 0 to 100% is recorded for each species as percent control with 0% representing no injury and 100% representing complete control.

Several compounds were evaluated at an application rate of 0.17 kg/ha for pre- and post-emergence activity against the same weed species that are used in the above-described pre-emergent multi-herbicide test.

The process was generally similar to the pre-emergence herbicide test procedure described above except that only 17 milligrams of test compound were weighted out.

The results of the 0.25 kg/ha pre-emergence test are shown in Table II. The results of the 0.17 kg/ha pre-emergence test are shown in the following Table IV.

TABLE II

Pre-emergence Herbicidal Activity
Application Rate - 0.25 kg/ha

| Compd. No. | GFT | FT | WG | BSG | AMG | CB | VL | YNS |
|---|---|---|---|---|---|---|---|---|
| 1 | 100 | — | 100 | 100 | 100 | 100 | 100 | 98 |
| 2 | 50 | 0 | 0 | 10 | 0 | 0 | 80 | 0 |
| 5 | 30 | 40 | — | 85 | 5 | 20 | 100 | 50 |

(—) = Not tested.

Post-emergence Multi-weed Herbicide Test: This test is conducted in an identical manner to the testing procedure for the pre-emergence multi-weed herbicide test, except the seeds of the eight different weed species are planted 10–12 days before treatment. Also, watering of the treated flats is confined to the soil surface and not to the foliage of the sprouted plants.

The results of the post-emergence multi-weed herbicide test are reported in Tables III and V.

TABLE III

Post-emergence Multi-weed Herbicidal Activity
Application Rate - 0.25 kg/ha

| Compd. No. | GFT | FT | WG | BSG | AMG | CB | VL | YNS |
|---|---|---|---|---|---|---|---|---|
| 1 | 80 | — | 100 | 95 | 100 | 90 | 100 | 70 |
| 2 | 0 | 0 | 60 | 5 | 5 | 10 | 85 | 0 |
| 5 | 15 | 60 | 85 | 60 | 85 | 95 | 85 | 50 |

TABLE IV

Pre-emergence Herbicidal Activity
Application Rate - 0.17 kg/ha

| Compd. No. | GTF | FT | WG | BSG | AMG | CB | VL | YNS |
|---|---|---|---|---|---|---|---|---|
| 3 | 100 | 100 | 100 | 100 | 70 | 90 | 100 | 98 |
| 4 | 50 | 90 | 100 | 50 | 60 | 100 | 100 | 98 |

TABLE V

Post-emergence Herbicidal Activity
Application Rate - 0.17 kg/ha

| Compd. No. | GTF | FT | WG | BSG | AMG | CB | VL | YNS |
|---|---|---|---|---|---|---|---|---|
| 3 | 100 | 100 | 100 | 100 | 70 | — | 100 | 50 |
| 4 | 20 | 20 | 95 | 100 | 100 | — | 100 | 30 |

(—) = Not tested.

The compounds of the present invention are useful as herbicides and can be applied in a variety of ways at various concentrations. In practice, the compounds herein defined are formulated into herbicidal compositions, by admixture, in herbicidally effective amounts, with the adjuvants and carriers normally employed for facilitating the dispersion of active ingredients for agricultural applications, recognizing the fact that the formulation and mode of application of a toxicant may affect the activity of the materials in a given application. Thus, these active herbicidal compounds may be formulated as granules of relatively large particle size, as wettable powders, as emulsifiable concentrates, as powdery dusts, as solutions or as any of several other known types of formulations, depending upon the desired mode of application. Preferred formulations for pre-emergence herbicidal applications are wettable powders, emulsifiable concentrates and granules. These formulations may contain as little as about 0.5% to as much as about 95% or more by weight of active ingredient. A herbicidally effective amount depends upon the nature of the seeds or plants to be controlled and the rate of application varies from about 0.05 to approximately 10 pounds per acre, preferably from about 0.1 to about 4 pounds per acre.

Wettable powders are in the form of finely divided particles which disperse readily in water or other dispersants. The wettable powder is ultimately applied to the soil either as a dry dust or as a dispersion in water or other liquid. Typical carriers for wettable powders include fuller's earth, kaolin clays, silicas and other readily wet organic or inorganic diluents. Wettable powders normally are prepared to contain about 5% to about 95% of the active ingredient and usually also contain a small amount of wetting, dispersing, or emulsifying agent to facilitate wetting and dispersion.

Emulsifiable concentrates are homogeneous liquid compositions which are dispersible in water or other dispersant, and may consist entirely of the active compound with a liquid or solid emulsifying agent, or may also contain a liquid carrier, such as xylene, heavy aromatic naphthal, isophorone and other non-volatile organic solvents. For herbicidal application, these concentrates are dispersed in water or other liquid carrier and normally applied as a spray to the area to be treated. The percentage by weight of the essential active ingredient may vary according to the manner in which the composition is to be applied, but in general comprises about 0.5% to 95% of active ingredient by weight of the herbicidal composition.

Granular formulations wherein the toxicant is carried on relatively coarse particles, are usually applied without dilution to the area in which suppression of vegetation is desired. Typical carriers for granular formulations include sand, fuller's earth, bentonite clays, vermiculite, perlite and other organic or inorganic materials which absorb or which may be coated with the toxicant. Granular formulations normally are prepared to contain about 5% to about 25% of active ingredients which may include surface-active agents such heavy aromatic naphthas, kerosene or other petroleum fractions, or vegetable oils; and/or stickers such as dextrins, glue or synthetic resins.

Typical wetting, dispersing or emulsifying agents used in agricultural formulations include, for example, the alkyl and alkylaryl sulfonates and sulfates and their sodium salts; polyhydric alcohols; and other types of surface-active agents, many of which are available in commerce. The surface-active agent, when used, normally comprises from 0.1% to 15% by weight of the herbicidal compositions.

Dusts, which are free-flowing admixtures of the active ingredient with finely divided solids such as talc, clays, flours and other organic and inorganic solids which act as dispersants and carriers for the toxicant, are useful formulations for soil-incorporating application.

Pastes, which are homogeneous suspensions of a finely divided solid toxicant in a liquid carrier such as water or oil, are employed for specific purposes. These formulations normally contain about 5% to about 95% of active ingredient by weight, and may also contain small amounts of a wetting, dispersing or emulsifying agent to facilitate dispersion. For application, the pastes are normally diluted and applied as a spray to the area to be affected.

Other useful formulations for herbicidal applications include simple solutions of the active ingredient in a dispersant in which it is completely soluble at the desired concentration, such as acetone, alkylated naphthalenes, xylene and other organic solvents. Pressurized sprays, typically aerosols, wherein the active ingredient is dispersed in finely-divided form as a result of vaporization of a low boiling dispersant solvent carrier, such as the Freons, may also be used.

The phytotoxic compositions of this invention are applied to the plants in the conventional manner. Thus, the dust and liquid compositions can be applied to the plant by the use of power-dusters, boom and hand sprayers and spray dusters. The compositions can also be applied from airplanes as a dust or a spray because they are effective in very low dosages. In order to modify or control growth of germinating seeds or emerging seedlings, as a typical example, the dust and liquid compositions are applied to the soil according to conventional methods and are distributed in the soil to a depth of at least ½ inch below the soil surface. It is not necessary that the phytotoxic compositions be admixed with the soil particles since these compositions can also be applied merely by spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging or mixing operations.

| EMULSIFIABLE CONCENTRATE FORMULATIONS | | | |
|---|---|---|---|
| General Formula with Ranges | | Specific Formula | |
| herbicidal compound | 5-55 | herbicidal compound | 54 |
| surfactant(s) | 5-25 | proprietary blend of oil- | 10 |
| solvent(s) | 20-90 | soluble sulfonates and | |
| | 100% | polyoxyethylene ethers | |
| | | polar solvent | 27 |
| | | petroleum hydrocarbon | 9 |
| | | | 100% |

| WETTABLE POWDER FORMULATIONS | | | |
|---|---|---|---|
| herbicidal compound | 3-90 | herbicidal compound | 80 |
| wetting agent | 0.5-2 | sodium dialkyl | 0.5 |
| dispersing agent | 1-8 | naphthalene sulfonate | |
| diluent(s) | 8.5-87 | sodium lignosulfonate | 7 |
| | 100% | attapulgite clay | 12.5 |
| | | | 100% |

| EXTRUDED GRANULAR FORMULATIONS | | | |
|---|---|---|---|
| herbicidal compound | 1-20 | herbicidal compound | 10 |
| binding agent | 0-10 | lignin sulfonate | 5 |
| diluent(s) | 70-99 | calcium carbonate | 85 |
| | 100% | | 100% |

| FLOWABLE FORMULATIONS | | | |
|---|---|---|---|
| herbicidal compound | 20-70 | herbicidal | 45 |
| surfactant(s) | 1-10 | compound | |
| suspending agent(s) | 0.05-1 | polyoxyethylene | 5 |
| antifreeze agent | 1-10 | ether | |
| antimicrobial agent | 1-10 | attagel | 0.05 |
| antifoam agent | 0.1-1 | propylene glycol | 10 |
| solvent | 7.95-76.85 | BIT | 0.03 |
| | 100% | silicone defoamer | 0.02 |
| | | water | 39.9 |
| | | | 100% |

The phytotoxic compositions of this invention can also contain other additives, for example, fertilizers, other herbicides and other pesticides, used as adjuvant or in combination with any of the above-described adjuvants. Fertilizers useful in combination with the active ingredients include, for example, ammonium nitrate, urea and superphosphate.

The herbicidal compounds of this invention can be used in combination with other herbicidal compounds for broader spectrum control of undesirable vegetation. Examples of other herbicidal compounds are as follows:
1. Anilides
Alachlor—2-chloro-2′, 6′-diethyl-N-(methoxymethyl)acetanilide
Metolachlor—2-chloro-2′-methyl-6′ethyl-N-methoxyisopropyl-2-acetanilide
Propanil—N-(3,4-dichlorophenyl)propionanilide
Acetachlor—2-chloro-2′-methyl-6′ethyl-N-ethoxymethylacetanilide
2. Triazines
Atrazine—2-chloro-4-(ethylamino)-6-isopropylamino)-s-triazine
Cyanazine—2-chloro-4-(1-cyano-1-methylethylamino)-6-ethylamino-s-triazine
Metribuzin—4-amino-6-tert-butyl-3-(methylthio) -1,2,4-triazin-5(4H)-one
3. Thiocarbamates
Molinate—S-ethyl hexahydro-1H-azepine-1-carbothioate
Butylate—S-ethyl diisobutylthiocarbamate
4. Ureas
Monuron—3-(p-chlorophenyl)-1,1-dimethylurea
Linuron—3-(3,4-dichlorophenyl)-1-methoxy-1-methylurea
5. Toluidines
Trifluralin—α,α,α-trifluoro-2,6-dinitro-N, N-dipropyl-p-toluidine
Pendimethalin—N-(1-ethylpropyl)-3,4-dimethyl-2, 6-dinitrobenzeneamine
6. Hormones
2,4-D—(2,4-dichlorophnoexy) acetic acid
MCPA—(2-methyl-4-chlorophenoxy) acetic acid
7. Diazines
Bentazon—3-isopropyl-1H-2,3,1-benzothiadiazin-4(3H)-one 2,2-dioxide
Oxadiazon—2-tert-butyl-4-(2,4-dichloro-5-isopropoxyphenyl)-$\Delta^2$-1,3,4-oxadiazolin-5-one 8. Diphenyl ethers
Acifluorfen—sodium 5-[2-chloro-4-(trifluoromethyl)-phenoxy]-2-nitrobenzoate
Fluazifop—butyl -(±)-butyl 2-[4[(5-(trifluoromethyl)-2-pyridinyl)oxy]phenoxy]propanoate pyridinyl)oxy]phenoxy]propanoate
Chlomethoxynil—2,4-dichlorophenyl 3-methoxy-4-nitrophenyl ether 9. Imidazolinones
Imazaquin—2-[4,5-dihydro-4-methyl-4-(1-methylethyl)-5-oxo-1H-imidazol-2-yl]-3-quinolin carboxylic acid 10. Sulfonyl ureas
Bensulfuron methyl—methyl 2-[[[[[(4, 6-dimethoxypyrimidin-2-yl)amino]carbonyl]amino]sulfonyl]methyl]benzoate
Chlorimuron ethyl—ethyl 2-(((((4-chloro-6-methoxypyrimidin-2-yl)amino)carbonyl)amino)sulfonyl)benzoate 11. 2-(2-Substituted benzoyl)-1,3-cyclohexanediones
2- (2'-chloro-4-methysulfonyl benzoyl)-1', 3-cyclohexanedione 12. Miscellaneous compounds
Dimethazone—2-(2-chlorophenyl)methyl-4, 4-dimethyl-3-isoxazolidinone
Norflurazon—4-chloro-5-(methylamino)-2-α, α,α-trifluoro-m-tolyl)-3-(2H)-pyridazinone
Dalapon—2,2-dichloropropionic acid
Glyphosate—isopropyl amine salt of N-(phosphonomethyl) glycine
Fenoxaprop-ethyl—(+)-ethyl-2,4-((6-chloro-2-benzoxazoly loxy)phenoxy)propanoate

What is claimed is:

1. A compound of the formula wherein
R is halogen, $C_1$-$C_2$ alkyl, $C_1$-$C_2$ alkoxy, nitro; cyano; $C_1$-$C_2$ haloalkyl, or $R^aSO_n$—wherein n is 0 or 2 and $R^a$ is $C_1$-$C_2$ alkyl;
$R^1$ is hydrogen or $C_1$-$C_4$ alkyl;
$R^2$ is hydrogen or $C_1$-$C_2$ alkyl; or
$R^1$ and $R^2$ together are alkylene having 2 to 5 carbon atoms;
$R^3$ is hydrogen or $C_1$-$C_4$ alkyl;
$R^4$ is hydrogen or $C_1$-$C_4$ alkyl; or
$R^3$ and $R^4$ together are oxo;
$R^5$ is hydrogen or $C_1$-$C_4$ alkyl;
$R^6$ is hydrogen or $C_1$-$C_4$ alkyl; or
$R^5$ and $R^6$ together are alkylene having 2 to 5 carbon atoms;
$R^7$ and $R^8$ independently are (1) hydrogen; (2) halogen; (3) $C_1$-$C_4$ alkyl; (4) $C_1$-$C_4$ alkoxy; (5) trifluoromethoxy; (6) cyano; (7) nitro; (8) $C_1$-$C_4$ haloalkyl; (9) $R^bSO_n$—wherein n is the integer 0, 1 or 2; and $R^b$ is (a) $C_1$-$C_4$ alkyl; (b) $C_1$-$C_4$ alkyl substituted with halogen or cyano; (c) phenyl; or (d) benzyl; (10) —$NR^cR^d$ wherein $R^c$ and $R^d$ independently are hydrogen or $C_1$-$C_4$ alkyl; (11) $R^eC(O)$— wherein $R^e$ is $C_1$-$C_4$ alkyl or $C_1$-$C_4$ alkoxy; (12) $SO_2NR^cR^d$ wherein $R^c$ and $R^d$ are as defined; (13) —$N(R^c)C(O)R^d$ wherein $R^c$ and $R^d$ are as defined; or (14) —$CH_2CH_2OCH_3$ or —$CH_2CH_2OC_2H_5$; with the proviso that $R^7$ is not at the 6-position; and
$R^9$ is hydrogen or $C_1$-$C_4$ alkyl; and
$R^{10}$ is $C_2$-$C_6$ alkylene, $C_4$-$C_8$ alkenylene or $C_4$-$C_8$ alkynylene with the proviso that $R^7$ is not at the 6-position.

2. The compounds of claim 1 wherein R is chlorine, bromine, $C_1$-$C_2$ alkyl, $C_1$-$C_2$ alkoxy, nitro, $C_1$-$C_2$ alkylthio or $C_1$-$C_2$ alkylsulfonyl; $R^1$ is hydrogen or methyl; $R^2$ is hydrogen or methyl; $R^3$ is hydrogen or methyl; $R^4$ is hydrogen or methyl; $R^5$ is hydrogen or methyl; $R^6$ is hydrogen or methyl; $R^7$ and $R^8$ independently are (1) hydrogen; (2) halogen; (3) $C_1$-$C_4$ alkyl; (4) $C_1$-$C_4$ alkoxy; (5) trifluoromethoxy; (6) cyano; (7) nitro; (8) $C_1$-$C_4$ haloalkyl; (9) $R^bSO_n$—wherein n is the integer 0, or 2; and $R^b$ is (a) $C_1$-$C_2$ alkyl; or (b) $C_1$-$C_2$ alkyl substituted with halogen or (10) —$CH_2CH_2OCH_3$ or —$CH_2CH_2OC_2H_5$; and $R^9$ is hydrogen or methyl and $R^{10}$ is $C_2$-$C_4$ alkylene.

3. The compound of claim 2 wherein $R^7$ is hydrogen, methylthio, methoxy, ethoxy, —$CH_2CH_2OCH_3$ or —$CH_2CH_2OC_2H_5$ and is in the 3-position, and $R^8$ is hydrogen, chlorine, bromine, fluorine, trifluoromethyl or $R^bSO_n$ wherein $R^b$ is $C_1$-$C_3$ alkyl and n is the integer 0 or 2.

4. The compound of claim 2 wherein R is chlorine; $R^1$ is hydrogen; $R^2$ is hydrogen; $R^3$ is hydrogen; $R^4$ is hydrogen; $R^5$ is hydrogen; $R^6$ is hydrogen; $R^7$ is hydrogen; $R^8$ is 4-methylsulfonyl; $R^9$ is methyl; and $R^{10}$ is ethylene.

5. The compound of claim 2 wherein R is nitro; $R^1$ is methyl; $R^2$ is methyl; $R^3$ is hydrogen; $R^4$ is hydrogen; $R^5$ is hydrogen; $R^6$ is hydrogen; $R^7$ is hydrogen; $R^8$ is hydrogen; $R^9$ is methyl; and $R^{10}$ is ethylene.

6. The compound of claim 2 wherein R is chlorine; $R^1$ is hydrogen; $R^2$ is hydrogen; $R^3$ is methyl; $R^4$ is hydrogen; $R^5$ is hydrogen; $R^6$ is hydrogen; $R^7$ is 3-ethoxy; $R^8$ is 4—$CH_3SO_2$—; and $R^9$ is methyl and $R^{10}$ is ethylene.

7. The compound of claim 2 wherein R is nitro; $R^1$ is methyl; $R^2$ is methyl; $R^3$ is hydrogen; $R^4$ is hydrogen; $R^5$ is hydrogen; $R^6$ is hydrogen; $R^7$ is hydrogen; $R^8$ is hydrogen; $R^9$ is methyl; and $R^{10}$ is ethylene.

8. The compound of claim 2 wherein R is nitro; $R^1$ is methyl; $R^2$ is methyl; $R^3$ is hydrogen; $R^4$ is hydrogen; $R^5$ is hydrogen; $R^6$ is hydrogen; $R^7$ is hydrogen; $R^8$ is 4-trifluoromethyl; $R^9$ is methyl; and $R^{10}$ is —$CH_2$—$CH=CH$—$CH_2$—.

9. The compound of claim 2 wherein R is nitro; $R^1$ is methyl; $R^2$ is methyl; $R^3$ is hydrogen; $R^4$ is hydrogen; $R^5$ is hydrogen; $R^6$ is hydrogen; $R^7$ is hydrogen; $R^8$ is 4—$CH_3SO_2$—; $R^9$ is methyl and $R^{10}$ is butylene.

10. The compound of claim 1 wherein R is nitro; $R^1$ is methyl; $R^2$ is methyl; $R^3$ and $R^4$ are oxo; $R^5$ is methyl; $R^6$ is methyl; $R^7$ is hydrogen; $R^8$ is 4-trifluoromethyl; $R^9$ is methyl; and $R^{10}$ is ethylene.

11. The method of controlling undesirable vegetation comprising applying to the area where control is desired, an herbicidally effective amount of a compound having the formula

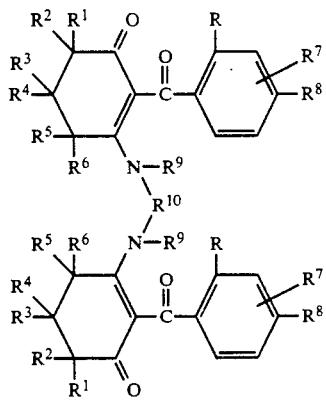

wherein
R is halogen, $C_1$-$C_2$ alkyl, $C_1$-$C_2$ alkoxy, nitro; cyano; $C_1$-$C_2$ haloalkyl, or $R^aSO_n$—wherein n is 0 or 2 and $R^a$ is $C_1$-$C_2$ alkyl;
$R^1$ is hydrogen or $C_1$-$C_4$ alkyl;
$R^2$ is hydrogen or $C_1$-$C_4$ alkyl; or
$R^1$ and $R^2$ together are alkylene having 2 to 5 carbon atoms;
$R^3$ is hydrogen or $C_1$-$C_4$ alkyl;
$R^4$ is hydrogen or $C_1$-$C_4$ alkyl; or
$R^3$ and $R^4$ together are oxo;
$R^5$ is hydrogen or $C_1$-$C_4$ alkyl;
$R^6$ is hydrogen or $C_1$-$C_4$ alkyl; or
$R^5$ and $R^6$ together are alkylene having 2 to 5 carbon atoms;
$R^7$ and $R^8$ independently are (1) hydrogen; (2) halogen; (3) $C_1$-$C_4$ alkyl; (4) $C_1$-$C_4$ alkoxy; (5) trifluoromethoxy; (6) cyano; (7) nitro; (8) $C_1$-$C_4$ haloalkyl; (9) $R^bSO_n$—wherein n is the integer 0, 1 or 2; and $R^b$ is (a) $C_1$-$C_4$ alkyl; (b) $C_1$-$C_4$ alkyl substituted with halogen or cyano; (c) phenyl; or (d) benzyl; (10) —$NR^cR^d$ wherein $R^c$ and $R^d$ independently are hydrogen or $C_1$-$C_4$ alkyl; (11) $R^eC(O)$—wherein $R^e$ is $C_1$-$C_4$ alkyl or $C_1$-$C_4$ alkoxy; (12) $SO_2NR^cR^d$ wherein $R^c$ and $R^d$ are as defined; (13) —$N(R^c)C(O)R^d$ wherein $R^c$ and $R^d$ are as defined; or (14) —$CH_2CH_2OCH_3$ or —$CH_2CH_2OC_2H_5$; with the proviso that $R^7$ is not at the 6-position; and
$R^9$ is hydrogen or $C_1$-$C_4$ alkyl; and
$R^{10}$ is $C_2$-$C_6$ alkylene, $C_4$-$C_8$ alkenylene or $C_4$-$C_8$ alkenylene 12. The method of claim 11 wherein R is chlorine, bromine, $C_1$-$C_2$ alkyl, $C_1$-$C_2$ alkoxy, nitro, $C_1$-$C_2$ alkylthio or $C_1$-$C_2$ alkylsulfonyl; $R^1$ is hydrogen or methyl; $R^2$ is hydrogen or methyl; $R^3$ is hydrogen or methyl; $R^4$ is hydrogen or methyl; $R^5$ is hydrogen or methyl; $R^6$ is hydrogen or methyl; $R^7$ and $R^8$ independently are (1) hydrogen; (2) halogen; (3) $C_1$-$C_4$ alkyl; (4) $C_1$-$C_4$ alkoxy; (5) trifluoromethoxy; (6) cyano; (7) nitro; (8) $C_1$-$C_4$ haloalkyl; (9) $R^bSO_n$—wherein n is the integer 0 or 2; and $R^b$ is (a) $C_1$-$C_2$ alkyl; or (b) $C_1$-$C_2$ alkyl substituted with halogen or (10) —$CH_2CH_2OCH_3$ or —$CH_2CH_2OC_2H_5$; and $R^9$ is hydrogen or methyl and $R^{10}$ is $C_2$-$C_4$ alkylene.

13. The method of claim 11 wherein R is chlorine; $R^1$ is hydrogen; $R^2$ is hydrogen; $R^3$ is hydrogen; $R^4$ is hydrogen; $R^5$ is hydrogen; $R^6$ is hydrogen; $R^7$ is hydrogen; $R^8$ is 4-methylsulfonyl; $R^9$ is methyl; and $R^{10}$ is ethylene.

14. The method of claim 12 wherein R is chlorine; $R^1$ is hydrogen; $R^2$ is hydrogen; $R^3$ is hydrogen; $R^4$ is hydrogen; $R^5$ is hydrogen; $R^6$ is hydrogen; $R^7$ is hydrogen; $R^8$ is 4-methylsulfonyl; $R^9$ is methyl; and $R^{10}$ is ethylene.

15. The method of claim 12 wherein R is nitro; $R^1$ is methyl; $R^2$ is methyl; $R^3$ is hydrogen; $R^4$ is hydrogen; $R^5$ is hydrogen; $R^6$ is hydrogen; $R^7$ is hydrogen; $R^8$ is hydrogen; $R^9$ is methyl; and $R^{10}$ is ethylene.

16. The method of claim 12 wherein R is chlorine; $R^1$ is hydrogen; $R^2$ is hydrogen; $R^3$ is methyl; $R^4$ is hydrogen; $R^5$ is hydrogen; $R^6$ is hydrogen; $R^7$ is 3-ethyloxy; $R^8$ is 4—$CH_3CH_2SO_2$—; $R^9$ is methyl and $R^{10}$ is ethylene.

17. The method of claim 12 wherein R is nitro; $R^1$ is methyl; $R^2$ is methyl; $R^3$ is hydrogen; $R^4$ is hydrogen; $R^5$ is hydrogen; $R^6$ is hydrogen; $R^7$ is hydrogen; $R^8$ is 4—$CH_3SO_2$—; $R^9$ is methyl; and $R^{10}$ is ethylene.

18. The method of claim 12 wherein R is nitro; $R^1$ is hydrogen; $R^2$ is hydrogen; $R^3$ is hydrogen; $R^4$ is hydrogen; $R^5$ is hydrogen; $R^6$ is hydrogen; $R^7$ is hydrogen; $R^8$ is 4-trifluoromethyl; $R^9$ is methyl; and $R^{10}$ is 2-butenethylene.

19. The method of claim 12 wherein R is nitro; $R^1$ is methyl; $R^2$ is methyl; $R^3$ is hydrogen; $R^4$ is hydrogen; $R^5$ is hydrogen; $R^6$ is hydrogen; $R^7$ is hydrogen; $R^8$ is 4—$CH_3SO_2$—; $R^9$ is methyl and $R^{10}$ is butylene.

20. The method of claim 11 wherein R is nitro; $R^1$ is methyl; $R^2$ is methyl; $R^3$ and $R^4$ are oxo; $R^5$ is methyl; $R^6$ is methyl; $R^7$ is hydrogen; $R^8$ is 4-trifluoromethyl; $R^9$ is methyl and $R^{10}$ is ethylene.

21. An herbicidal composition comprising an herbicidally active bis(2-benzoyl-3-oxo-cyclohexenyl)diamine.

22. An herbicidal composition comprising an herbicidally active compound having the structural formula

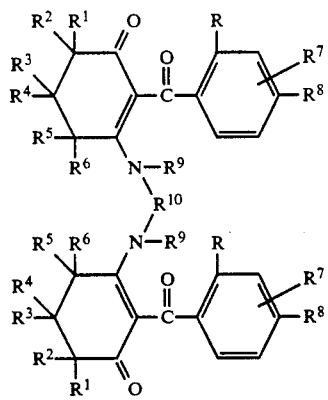

wherein
R is halogen, $C_1$-$C_2$ alkyl, $C_1$-$C_2$ alkoxy, nitro; cyano; $C_1$-$C_2$ haloalkyl, or $R^aSO_n$—wherein n is 0 or 2 and $R^a$ is $C_1$-$C_2$ alkyl;
$R^1$ is hydrogen or $C_1$-$C_4$ alkyl;
$R^2$ is hydrogen or $C_1$-$C_2$ alkyl; or
$R^1$ and $R^2$ together are alkylene having 2 to 5 carbon atoms;
$R^3$ is hydrogen or $C_1$-$C_4$ alkyl;
$R^4$ is hydrogen or $C_1$-$C_4$ alkyl; or
$R^3$ and $R^4$ together are oxo;
$R^5$ is hydrogen or $C_1$-$C_4$ alkyl;

$R^6$ is hydrogen or $C_1$-$C_4$ alkyl; or $R^5$ and $R^6$ together are alkylene having 2 to 5 carbon atoms;

$R^7$ and $R^8$ independently are (1) hydrogen; (2) halogen; (3) $C_1$-$C_4$ alkyl; (4) $C_1$-$C_4$ alkoxy; (5) trifluoromethoxy; (6) cyano; (7) nitro; (8) $C_1$-$C_4$ haloalkyl; (9) $R^bSO_n$—wherein n is the integer 0, 1 or 2; and $R^b$ is (a) $C_1$-$C_4$ alkyl; (b) $C_1$-$C_4$ alkyl substituted with halogen or cyano; (c) phenyl; or (d) benzyl; (10) —$NR^cR^d$ wherein $R^c$ and $R^d$ independently are hydrogen or $C_1$-$C_4$ alkyl; (11) $R^eC(O)$—wherein $R^e$ is $C_1$-$C_4$ alkyl or $C_1$-$C_4$ alkoxy; (12) $SO_2NR^cR^d$ wherein $R^c$ and $R^d$ are as defined; (13) —$N(R^c)C(O)R^d$ wherein $R^c$ and $R^d$ are as defined; or (14) —$CH_2CH_2OCH_3$ or —$CH_2CH_2OC_2H_5$; with the proviso that $R^7$ is not at the 6-position; and $R^9$ is hydrogen or $C_1$-$C_4$ alkyl; and $R^{10}$ is $C_2$-$C_6$ alkylene, $C_4$-$C_8$ alkenylene or $C_4$-$C_8$ alkynylene and an inert carrier therefor.

23. The composition of claim 22 wherein R is chlorine, bromine, $C_1$-$C_2$ alkyl, $C_1$-$C_2$ alkoxy, nitro, $C_1$-$C_2$ alkylthio or $C_1$-$C_2$ alkylsulfonyl; $R^1$ is hydrogen or methyl; $R^2$ is hydrogen or methyl; $R^3$ is hydrogen or methyl; $R^4$ is hydrogen or methyl; $R^5$ is hydrogen or methyl; $R^6$ is hydrogen or methyl; $R^7$ and $R^8$ independently are (1) hydrogen; (2) halogen; (3) $C_1$-$C_4$ alkyl; (4) $C_1$-$C_4$ alkoxy; (5) trifluoromethoxy; (6) cyano; (7) nitro; (8) $C_1$-$C_4$ haloalkyl; (9) $R^bSO_n$—wherein n is the integer 0 or 2; and $R^b$ is (a) $C_1$-$C_2$ alkyl; or (b) $C_1$-$C_2$ alkyl substituted with halogen or (10) —$CH_2CH_2OCH_3$ or —$CH_2CH_2OC_2H_5$; and $R^9$ is hydrogen or methyl and $R^{10}$ is $C_2$-$C_4$ alkylene.

24. The composition of claim 23 wherein $R^7$ is hydrogen, methylthio, methoxy, ethoxy, —$CH_2CH_2OCH_3$ or —$CH_2CH_2OC_2H_5$ and is in the 3-position, and $R^8$ is hydrogen, chlorine, bromine, fluorine, trifluoromethyl or $R^bSO_n$ wherein $R^b$ is $C_1$-$C_3$ alkyl and n is the integer 0 or 2.

25. The composition of claim 23 wherein R is chlorine; $R^1$ is hydrogen; $R^2$ is hydrogen; $R^3$ is hydrogen; $R^4$ is hydrogen; $R^5$ is hydrogen; $R^6$ is hydrogen; $R^7$ is hydrogen; $R^8$ is 4-methylsulfonyl; $R^9$ is methyl; and $R^{10}$ is ethylene.

26. The composition of claim 23 wherein R is nitro; $R^1$ is methyl; $R^2$ is methyl; $R^3$ is hydrogen; $R^4$ is hydrogen; $R^5$ is hydrogen; $R^6$ is hydrogen; $R^7$ is hydrogen; $R^8$ is hydrogen; $R^9$ is methyl; and $R^{10}$ is ethylene.

27. The composition of claim 23 wherein R is chlorine; $R^1$ is hydrogen; $R^2$ is hydrogen; $R^3$ is methyl; $R^4$ is hydrogen; $R^5$ is hydrogen; $R^6$ is hydrogen; $R^7$ is 3-ethoxy; $R^8$ is 4—$CH_3SO_2$—; and $R^9$ is methyl and $R^{10}$ is ethylene.

28. The composition of claim 23 wherein R is nitro; $R^1$ is methyl; $R^2$ is methyl; $R^3$ is hydrogen; $R^4$ is hydrogen; $R^5$ is hydrogen; $R^6$ is hydrogen; $R^7$ is hydrogen; $R^8$ is 4—$CH_3SO_2$—; $R^9$ is methyl; and $R^{10}$ is ethylene.

29. The composition of claim 23 wherein R is nitro; $R^1$ is methyl; $R^2$ is methyl; $R^3$ is hydrogen; $R^4$ is hydrogen; $R^5$ is hydrogen; $R^6$ is hydrogen; $R^7$ is hydrogen; $R^8$ is 4-trifluoromethyl; $R^9$ is methyl; and $R^{10}$ is —$CH_2$—$CH$=$CH$—$CH_2$—.

30. The composition of claim 23 wherein R is nitro; $R^1$ is methyl; $R^2$ is methyl; $R^3$ is hydrogen; $R^4$ is hydrogen; $R^5$ is hydrogen; $R^6$ is hydrogen; $R^7$ is hydrogen; $R^8$ is 4—$CH_3SO_2$—; $R^9$ is methyl and $R^{10}$ is butylene.

31. The composition of claim 22 wherein R is nitro; $R^1$ is methyl; $R^2$ is methyl; $R^3$ and $R^4$ are oxo; $R^5$ is methyl; $R^6$ is methyl; $R^7$ is hydrogen; $R^8$ is 4-trifluoromethyl; $R^9$ is methyl; and $R^{10}$ is ethylene.

* * * * *